(12) United States Patent
Müller (10) Patent No.: US 11,865,317 B2
(45) Date of Patent: Jan. 9, 2024

(54) DRIVE MECHANISM

(71) Applicant: SHL MEDICAL AG, Zug (CH)

(72) Inventor: Stephan Müller, Hemishofen (CH)

(73) Assignee: SHL MEDICAL AG, Zug (CH)

( * ) Notice: Subject to any disclaimer, the term of this patent is extended or adjusted under 35 U.S.C. 154(b) by 642 days.

(21) Appl. No.: 16/950,585

(22) Filed: Nov. 17, 2020

(65) Prior Publication Data
US 2021/0178077 A1  Jun. 17, 2021

(30) Foreign Application Priority Data

Dec. 11, 2019 (EP) ..................................... 19215189

(51) Int. Cl.
| | |
|---|---|
| *A61M 5/315* | (2006.01) |
| *A61M 5/20* | (2006.01) |
| *A61M 15/00* | (2006.01) |
| *A61M 11/00* | (2006.01) |

(52) U.S. Cl.
CPC ............ *A61M 5/3158* (2013.01); *A61M 5/20* (2013.01); *A61M 5/2033* (2013.01); *A61M 5/2046* (2013.01); *A61M 11/00* (2013.01); *A61M 15/00* (2013.01)

(58) Field of Classification Search
CPC .... A61M 5/3158; A61M 5/20; A61M 5/2033; A61M 5/2046; A61M 11/00; A61M 15/00; A61M 5/46; A61M 2005/2403; A61M 5/315; A61M 2005/3152
See application file for complete search history.

(56) References Cited

U.S. PATENT DOCUMENTS

| | | | |
|---|---|---|---|
| 2006/0258990 A1* | 11/2006 | Weber ..................... | A61M 5/20 604/208 |
| 2014/0012229 A1 | 1/2014 | Bokelman et al. | |
| 2014/0257241 A1 | 9/2014 | Sutkin et al. | |
| 2017/0197038 A1* | 7/2017 | Morlok ................. | A61M 5/321 |

FOREIGN PATENT DOCUMENTS

| | | |
|---|---|---|
| FR | 2767479 A1 | 2/1999 |
| WO | 2018/005915 A1 | 1/2018 |

\* cited by examiner

*Primary Examiner* — Emily L Schmidt
*Assistant Examiner* — Nelson Louis Alvarado, Jr.
(74) *Attorney, Agent, or Firm* — McDonnell Boehnen Hulbert & Berghoff LLP (57) ABSTRACT

A drive mechanism for a medicament delivery device is disclosed having a housing with a proximal end and a distal end, a container carrier arranged within the housing and being axially movable in relation to the housing, and a drive assembly partially arranged within the housing and being axially movable in relation to the housing. The drive assembly has a proximally extended rack arm, a cogwheel arranged within the housing and being rotatable but axially fixed in relation to the housing, wherein the cogwheel is selectively coupled to the rack arm through a tangential engagement with a first set of rack teeth or a second set of rack teeth which are arranged on the rack arm and wherein the first set of rack teeth or the second set of rack teeth forces the cogwheel to rotate when the drive assembly is axially moved towards the proximal end in relation to the housing. The cogwheel further has a connecting member configured to connect to a counter connecting member which is arranged on the container carrier; such that a rotational movement of the cogwheel is converted into a linear movement of the container carrier.

20 Claims, 10 Drawing Sheets

DRIVE MECHANISM

CROSS REFERENCE TO RELATED APPLICATIONS

The present application claims priority to European Patent Application No. 19215189.2 filed Dec. 11, 2019, which is herewith incorporated by reference into the present application.

TECHNICAL AREA

The present application relates to a drive mechanism for a medicament delivery device.

BACKGROUND

Medicament delivery devices such as auto-injectors, safety syringes, pen-injectors, inhalers, on-body devices are generally known for the self administration of a medicament by patients without formal medical training occurs. As just one example, those patients suffering from diabetes may require repeated injections of insulin. Other patients may require regular injections of other types of medicaments, such as a growth hormone or biological medicaments. Therefore, to facilitate for the patients, there is a demand to design medicament delivery devices with multiple automatic functions, predetermined dosage and assembled a medicament container.

To simplify the medicament delivery operation sequence, most of medicament delivery devices in the market are designed with multiple functions related to the medicament delivery operation can be achieved by one or two simple actions from end users.

The document FR 2767479 discloses an injection device comprising a syringe a rod configured to empty a medicament contained in the syringe. The rod comprises a tongue and a tab selectively engaging with the body of the syringe; the rod further comprises a set of racks configured to engage with a pinion. The injection device further comprises a pusher comprising another two sets of racks configured to rotate the pinion when the pusher is axially displaced, such that the rod will therefore be axially displaced. When the first set of racks of the pusher interacts with the pinion and the tongue of the rod engages with the body of the syringe, the axially displacement of the rod moves the syringe forward and protruding from a housing of the injection device; when the second set of racks of the pusher interacts with the pinion, the axial displacement of the pusher oppositely rotates the pinion, the rod is therefore moved rearward. Until the tab of the rod engages with the body of the syringe, the rod engages and therefore moves the syringe retracting together with the rearward movement of the rod. Such that the sequence of needle penetration on the injection site, medicament delivery and the needle retraction from the injection site can be all done by one axial displacement of the pusher that initiated by the end user.

However, the arrangement as disclosed in FR 2767479 requires both the rod and the pusher to be longitudinally arranged with sets of racks which causes the injection device to become longer. It also requires two radially opposite arranged sets of racks on the pusher which causes the pusher to become wider, so as the injection device will then become wider. Further, the injector in FR 2767479 uses the rod to move forward the medicament container, so there might be a risk that the medicament starts to be delivered before the medicament delivery member reaches a proper position.

SUMMARY

The aim of the present disclosure is to solve or at least mitigate the problems of the prior art.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

An object of this disclosure is to provide a simple and reliable way of accidental activation prevention mechanism for a medicament delivery device.

According to an aspect of the disclosure, the object is achieved by a robust and reliable drive mechanism according to claim 1.

There is hence provided a drive mechanism for a medicament delivery device, comprising: a housing having a proximal end and a distal end; a container carrier arranged within the housing and being axially movable in relation to the housing; a drive assembly partially arranged within the housing and being axially movable in relation to the housing; and wherein the drive assembly comprises a proximally extended rack arm; a cogwheel arranged within the housing and being rotatable but axially fixed in relation to the housing; wherein the cogwheel is selectively coupled to the rack arm through a tangential engagement with a first set of rack teeth or a second set of rack teeth which are arranged on the rack arm; wherein the first set of rack teeth or the second set of rack teeth forces the cogwheel to rotate when the drive assembly is axially moved towards the proximal end in relation to the housing; wherein the cogwheel further comprises a connecting member configured to connect to a counter connecting member which is fixed to the container carrier; such that a rotational movement of the cogwheel is converted into a linear movement of the container carrier.

According to one embodiment, the drive assembly is rotationally fixed in relation to the housing.

According to one embodiment, the container carrier is moved towards the proximal end in relation to the housing when the cog wheel is rotated by the first set of rack teeth and is moved towards the distal end in relation to the housing when the cog wheel is rotated by the second set of rack teeth while the drive assembly is moved towards the proximal end in relation to the housing.

According to one embodiment, the connecting member is a protruded pin perpendicularly arranged in relation to the edge of the cogwheel; wherein the counter connecting member is a traverse recess; and wherein the protruded pin is arranged in the traverse recess.

According to one embodiment, the first set of rack teeth is discrete proximally arranged in relation to the second set of rack teeth.

According to one embodiment, the drive assembly further comprises a user accessible pushing element; such that the proximally axial movement of the drive assembly is created by a manually proximal pushing action applied onto the pushing element by the user.

According to one embodiment, the drive assembly is axially biased in the proximal direction by a drive unit.

According to one embodiment, the first set of rack teeth and the second set of rack teeth are arranged to rotate the cogwheel in the same rotation direction.

According to one embodiment, the drive mechanism is included in a medicament delivery device.

According to one embodiment, the medicament delivery device comprises a medicament container arranged with a medicament delivery member on its proximal end and contained a medicament therein; wherein the medicament container is axially fixed to the container carrier; and wherein the medicament container comprises a plunger configured to be moved towards the proximal end to expel the contained medicament through the medicament delivery member.

According to one embodiment, the drive assembly further comprises a plunger holder associated with the stopper of the medicament container; wherein the proximal movement of the drive assembly moves the plunger towards the proximal end through the plunger holder.

According to one embodiment, the proximal movement of the drive assembly sequentially causes the first set of rack teeth rotate the cogwheel, the plunger moves proximally to expel the medicament and the second set of rack teeth rotate the cogwheel.

According to one embodiment, the rack arm, the user accessible pushing element and the plunger holder arranged on the drive assembly can be all formed as one single component, or as all separate components or some are integral together and some are separate components.

According to one embodiment, the medicament container can be a syringe arranged with a needle or a delivery nozzle; or a cartridge that can be attached with a needle or a delivery nozzle by an end user.

According to one embodiment, the medicament delivery device can be a safety syringe, an auto injector, a pen injector, an inhalation device, an on-body device or a medical sprayer.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE FIGURES

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
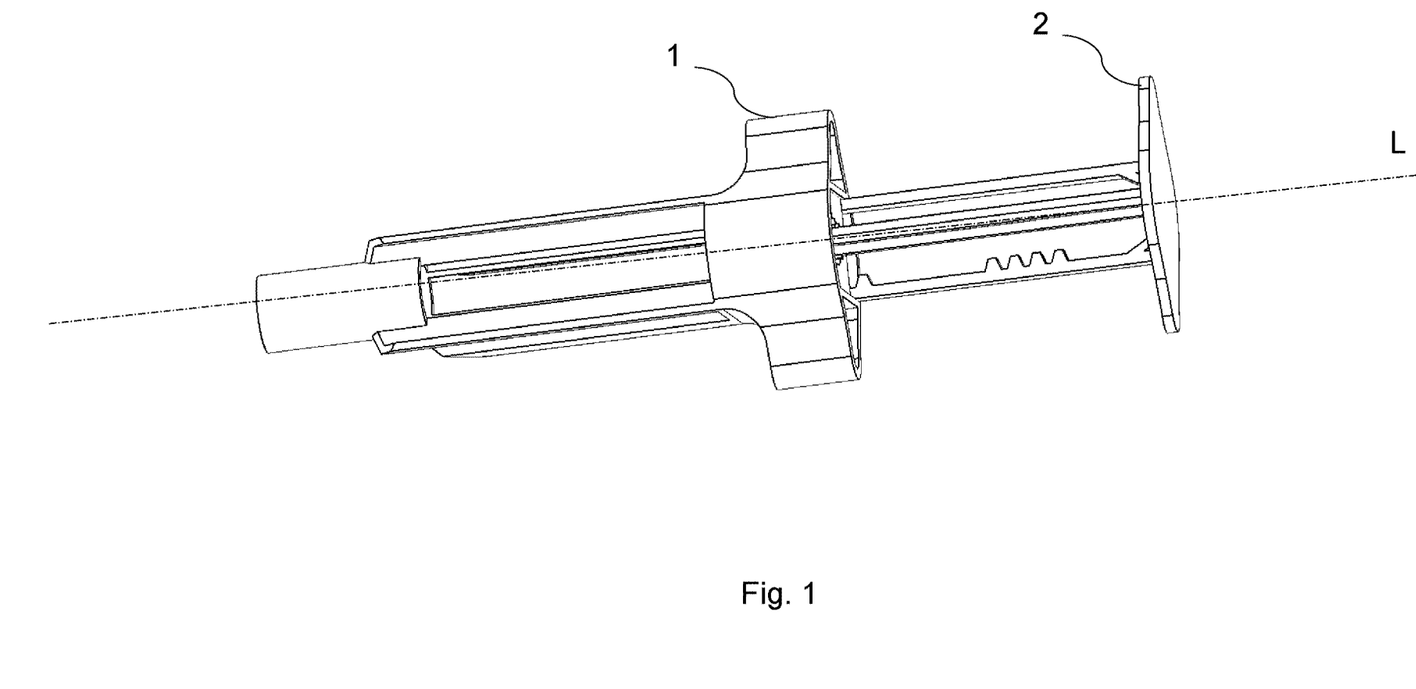
FIG. 1 displays a drive mechanism of the disclosure for a medicament delivery device.
Figure 2:
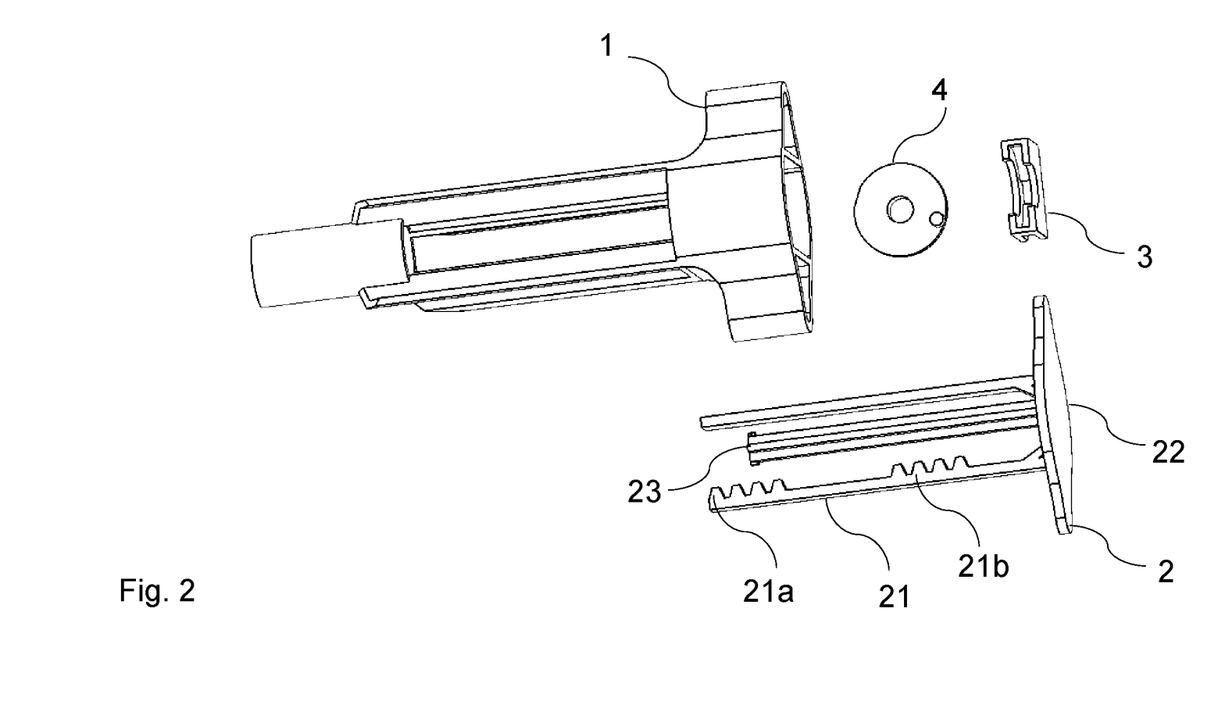
FIG. 2 displays an exploded view of the drive mechanism of FIG. 1.

FIG. 1 illustrates a drive mechanism for a medicament delivery device comprising: a housing 1 having a proximal end and a distal end; and a drive assembly 2 partially arranged within the housing 1. The housing 1 extends along a longitudinal axis L from the proximal end to the distal end. The drive assembly 2 is axially movable in relation to the housing 1 and along the longitudinal axis L. As shown in FIG. 2, the drive assembly 2 comprises a proximally extended rack arm 21, a user accessible pushing element 22 and a plunger holder 23. The proximally extended rack arm 21 comprises a first set of rack teeth 21a discrete proximally arranged in relation to a second set of rack teeth 21b. The drive mechanism further comprises a container carrier 3 and a cogwheel 4.

Figure 3A:
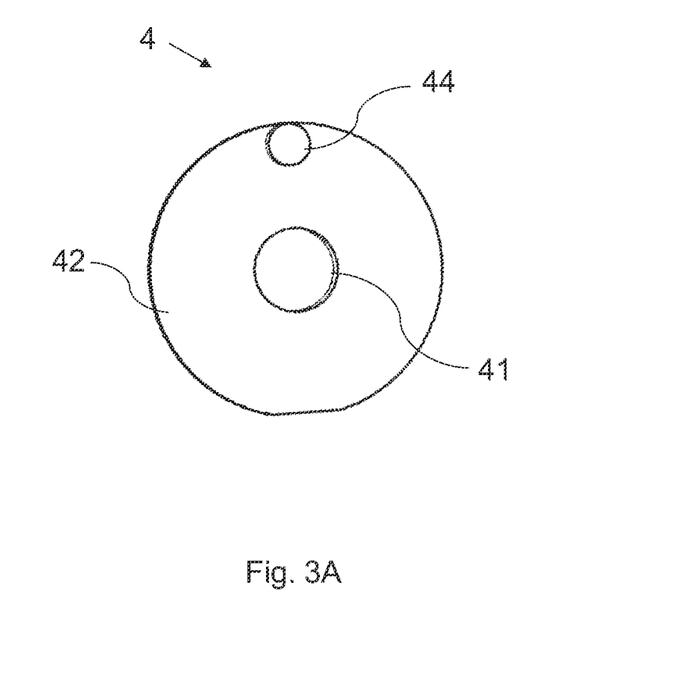
FIG. 3A displays the front and back view of a cogwheel of the drive mechanism of FIG. 1.
Figure 3B:
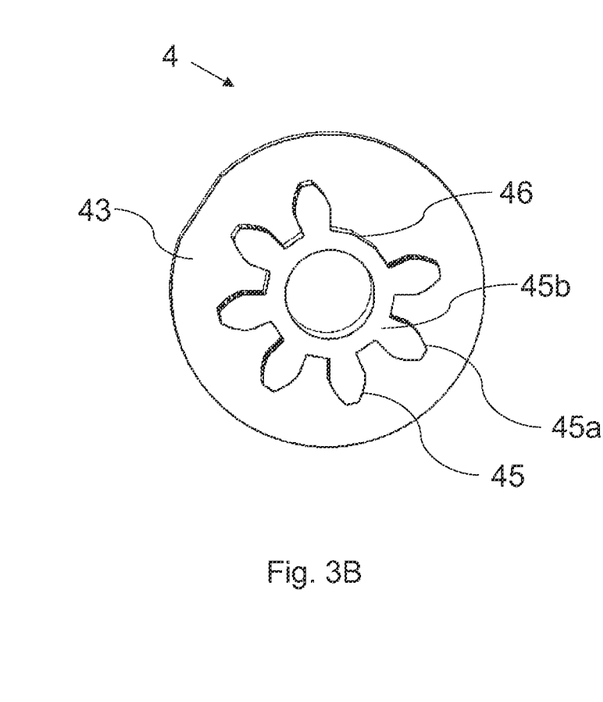
FIG. 3B displays the front and back view of a cogwheel of the drive mechanism of FIG. 1.

FIG. 3A-3B illustrate a front surface 42 and a back surface 43 of the cogwheel 4. The cogwheel 4 comprises a fixture 41 configured to axially fix but rotatably attached the cogwheel 4 to the housing 1, the fixture can be a central through opening or a backward protruded pin. The front surface 42 is arranged with a connecting member 44, preferably, it can be a front protruded pin radial inwardly protruding towards a central cavity of the housing 1. The back surface 43 of the cogwheel 4 is circularly arranged with plurality cogs 45. Each cog of the plurality cogs 45 comprises a thickness at least partially occupied the space defined by the back surface 43 of the cogwheel and the inner surface of the housing 1. Each cog of the plurality cogs 45 further comprises an engaging end 45a and a connecting end 45b. The connecting end 45b of each cog of the plurality cogs 45 is configured to couple to each other in a central portion of the back surface 43 of the cogwheel 4. The engaging end 45a of each cog of the plurality cogs 45 is configured to radial outwardly extend towards the outer edge of the back surface 43 of the cogwheel 4. The cogwheel 4 is selectively coupled to the rack arm 21 through a tangential engagement between the plurality cogs 45, more specifically the engaging end 45a of each cog of the plurality cogs 45, with the first set of rack teeth 21a or the second set of rack teeth 21b.

Further, the cogwheel 4 may optionally comprise a smooth portion 46. The smooth portion 46 is arranged between two cogs of the plurality cogs 45 and is configured to define a start and an end rotation position of the cogwheel 4, such that the cogwheel 4 is configured to be rotated by the rack arm 21 from one cog adjacent to the smooth portion 46, through the rest of the plurality cogs 45 to another cog adjacent to the smooth portion 46.

Figure 4A:
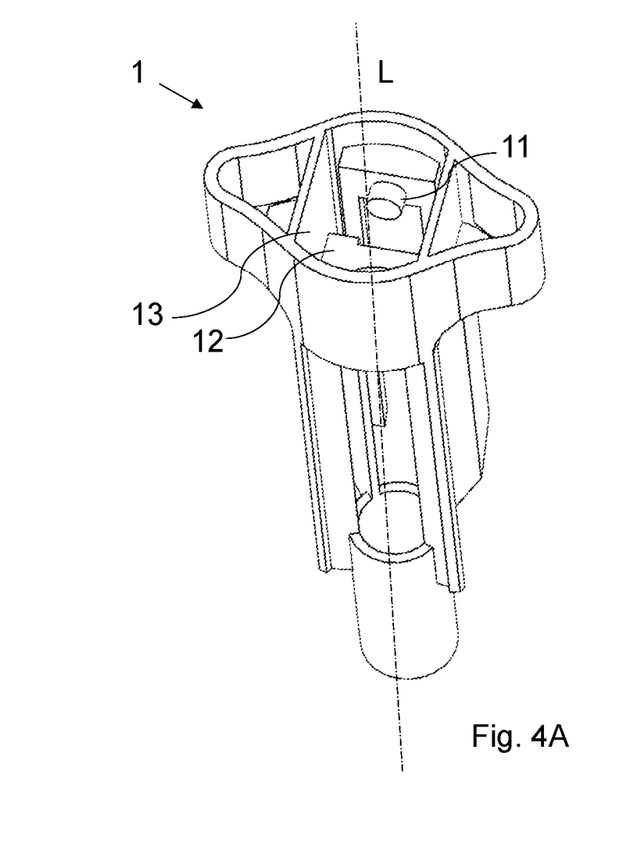
FIG. 4A displays a housing of the drive mechanism of FIG. 1.
Figure 4B:
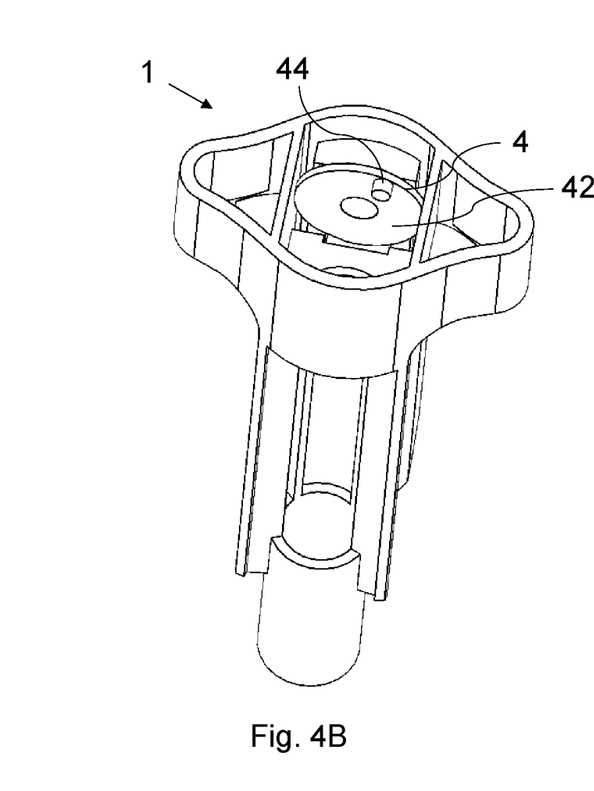
FIG. 4B displays the housing arranged with the cogwheel of the drive mechanism of FIG. 1.

FIG. 4A-4B illustrate the attachment between the housing 1 and the cogwheel 4. The housing 1 comprises a counter fixture 11, configured to engage with the fixture 41 of the cogwheel 4, preferably, the counter fixture 11 is an inwardly radial extending protrusion, as shown in FIG. 4A. When the cogwheel 4 is attached to the housing 1 as shown in the FIG. 4B, the front surface 42 of the cogwheel 4 faces the central cavity of the housing 1 which is configured to receive a medicament container 5.

Figure 5:
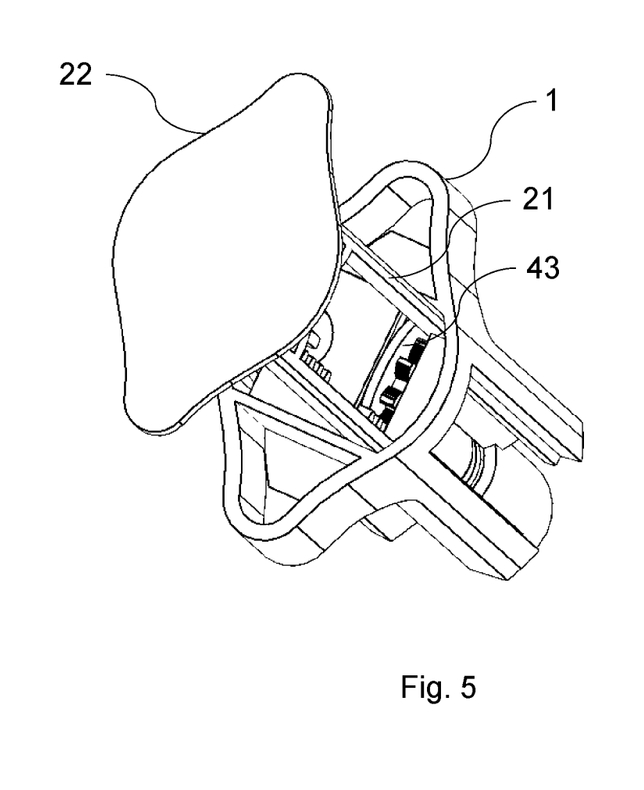
FIG. 5 displays the perspective view of the drive mechanism of FIG. 1.
Figure 6:
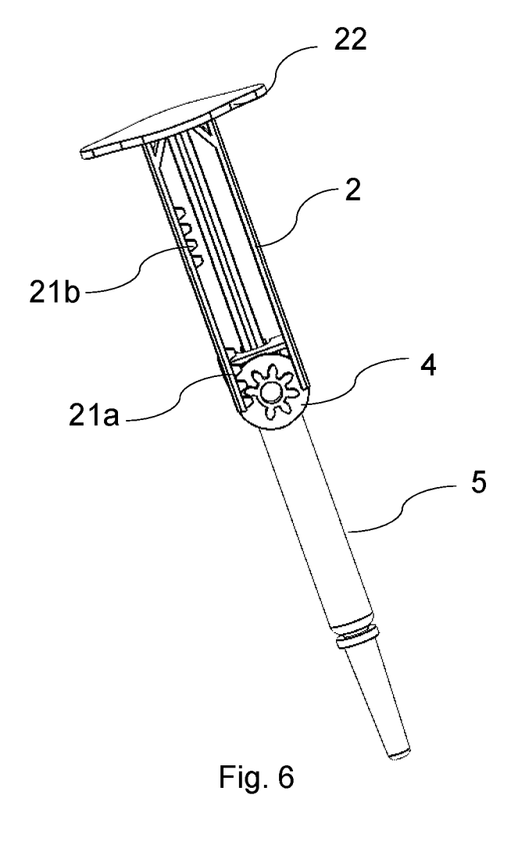
FIG. 6 displays a side view of the drive mechanism of FIG. 1. arranged with the medicament container and without the housing.

The rack arm 21 is configured to extend between the housing 1 and the back surface 43 of the cogwheel, as shown in FIG. 5. The first set of rack teeth 21a or the second set of rack teeth 21b are selectively engaged with the plurality cogs 45, such that an axial movement of the drive assembly 2 in relation to the housing 1 causes the first set of rack teeth 21a or the second set of rack teeth 21b to rotate the cogwheel 4 when the first set of rack teeth 21a or the second set of rack teeth 21b are engaged with the plurality cogs 45, as shown in FIG. 6.

Figure 7:
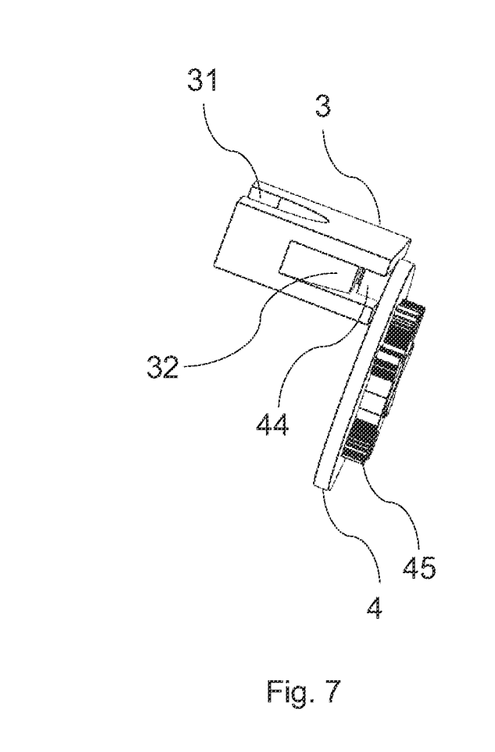
FIG. 7 displays a container carrier arranged with the cogwheel of the drive mechanism of FIG. 1.
Figure 8:
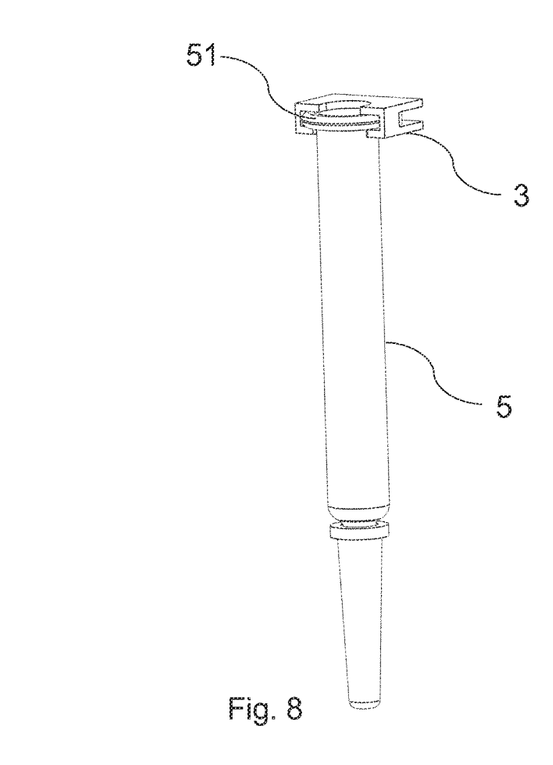
FIG. 8 displays a medicament container arranged with the container carrier of the drive mechanism of FIG. 1.

The connecting member 44 of the cogwheel 4 is configured to connect to a counter connecting member 32, which is arranged on the container carrier 3, as shown in FIG. 7, preferably, the counter connecting member 32 is a transverse recess in relation to the longitudinal axis L. The container carrier 3 further comprises a retainer 31, which is configured to receive and hold a flange 51 of the medicament container 5, as shown in FIG. 8. The housing 1 may optionally comprise an inner support 12 and an inner wall 13, as shown in FIG. 4A. The inner wall 13 is configured to prevent the radial movement and the rotation movement of the container carrier 3. The inner support 12 is radial inwardly extending from the inner wall towards the central cavity of the housing 1. The inner support 12 defines a central passage with a dimension that is larger than the radial dimension of the medicament container but smaller than the radial dimension of the container carrier 3, such that the medicament container 5 is able to at least partially pass through the central passage, and the container carrier 3 is configured to be supported by the inner support 12 at its proximal position.

It should be noted that, alternatively, the connecting member 44 can be a transverse recess or a transverse curve recess in relation to the longitudinal axis L; and the counter connecting member 32 can be a radial outwardly protruding pin configured to engage with the transverse recess or the transverse curve recess of the connecting member 44. Further, the retainer 31 can be arranged to receive the flange of the medicament container 5, a distal portion of the medicament container or to receive a tubular main body of the medicament container 5.

Since the counter connecting member 32 is the transverse recess, when the cogwheel 4 rotates, the connecting member 44 will gradually press on an edge of the transverse recess, such that the container carrier 3 is moved axially by the connecting member 44. A rotational movement of the cogwheel 4 is therefore converted into a linear movement of the container carrier 3.

Figure 9A:
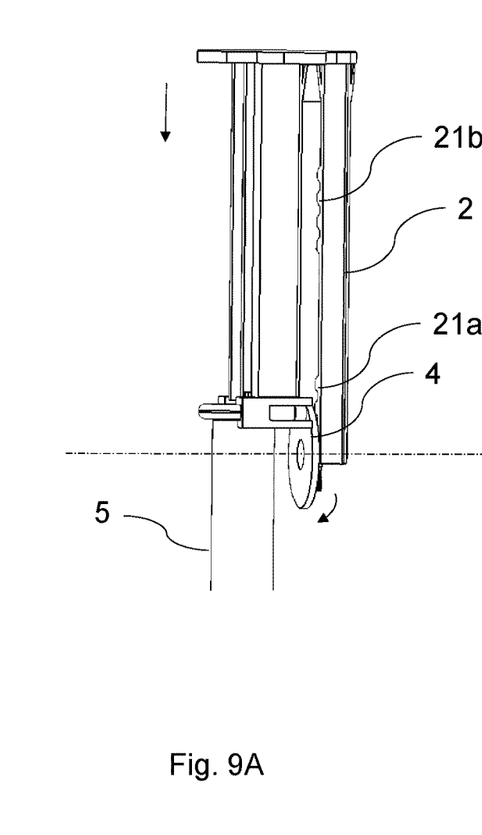
FIG. 9A displays the operation sequence of the drive mechanism of FIG. 1 without the housing.
Figure 9B:
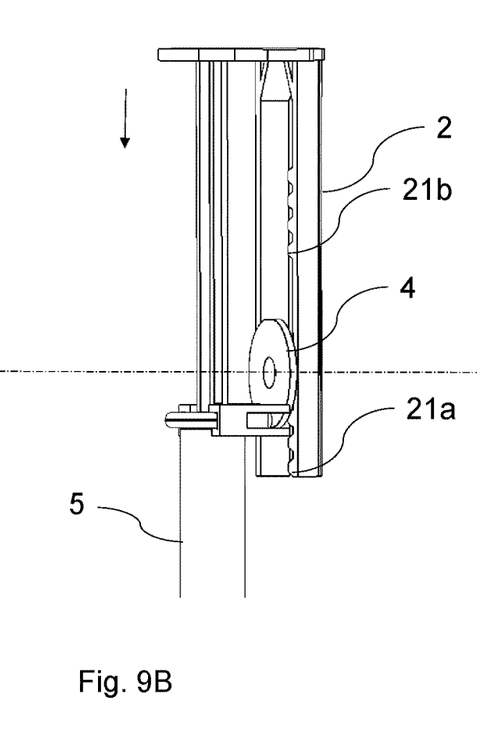
FIG. 9B displays the operation sequence of the drive mechanism of FIG. 1 without the housing.
Figure 9C:
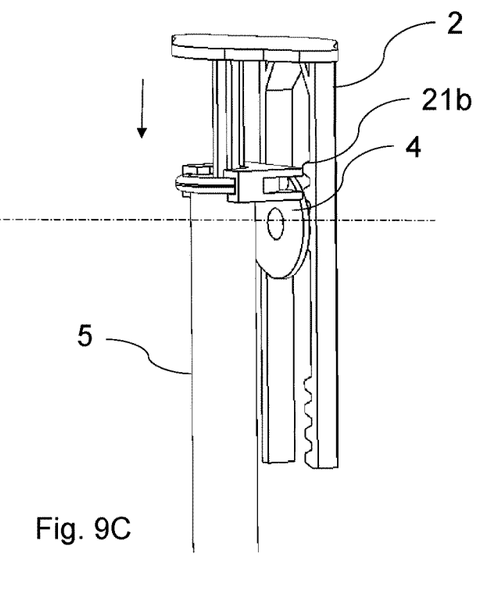
FIG. 9C displays the operation sequence of the drive mechanism of FIG. 1 without the housing.

The operation sequence of the drive mechanism of the disclosure is shown in FIG. 9A-9C. The dash line acts as a reference that indicates the position of the fixture 41 of the cogwheel 4 in FIG. 9A-9C. FIG. 9A illustrates the medicament container 5 in an axial initial position. To move the medicament container 5 in the proximal direction in relation to the housing 1, the drive assembly 2 is axially moved to the proximal direction in relation to the housing 1. When the first set of rack teeth 21a on the rack arm 21 is moved into an engagement with the plurality cogs 45, the axial movement of the first set of rack teeth 21a rotates the cogwheel 4. Due to the connection between the connecting member 44 of the cogwheel 4 and the counter connecting member 32 of the container carrier 3, the rotation movement of the cogwheel 4 turns into the axial movement of the container carrier 3 and the medicament container 5, such that the medicament container is moved to its proximal position as shown in FIG. 9B. The axial moving distance of the medicament container 5 may be defined by the diameter of the cogwheel 4 or the diameter of the circular moving path of the connecting member 44 associated with the inner support 12 of the housing 1. When the medicament container 5 has been moved into its proximal position, a medicament delivery operation may start. During the medicament delivery operation, the rack arm 21 is decoupled from the cogwheel 4 as none of the first set of rack teeth 21a or the second set of rack teeth 21b is engaged with the plurality cogs 45; the rack arm 21 is therefore prevented to rotate the cogwheel 4 with its axial movement.

After the medicament delivery operation is completed, the continuously axial movement of the drive assembly 2 causes the second set of rack teeth 21b to rotate the cogwheel 4. The rotation direction of the cogwheel 4 caused by the first set of rack teeth 21a is preferably the same as the rotation direction of the cogwheel 4 that is caused by the second set of rack teeth 21b; therefore, the cogwheel 4 would be rotated about one complete circle by the first set of rack teeth 21a and the second set of rack teeth 21b. The connecting member 44 of the cogwheel 4 is thereby rotated with the cogwheel 4 from its most distal position to its most proximal position by the axial movement of first set of rack teeth 21a; and rotated with the cogwheel 4 from its most proximal position back to its most distal position by the axial movement of second set of tack teeth 21b. Due to the connection between the connecting member 44 and the counter connecting member 32 as mentioned above, the rotation of the cogwheel 4 by the second set of rack teeth 21b axially moved the container carrier 3 so as the medicament container 5 back to its initial position, as shown in FIG. 9C at the end of the medicament delivery operation.

Figures 10A, 10B:
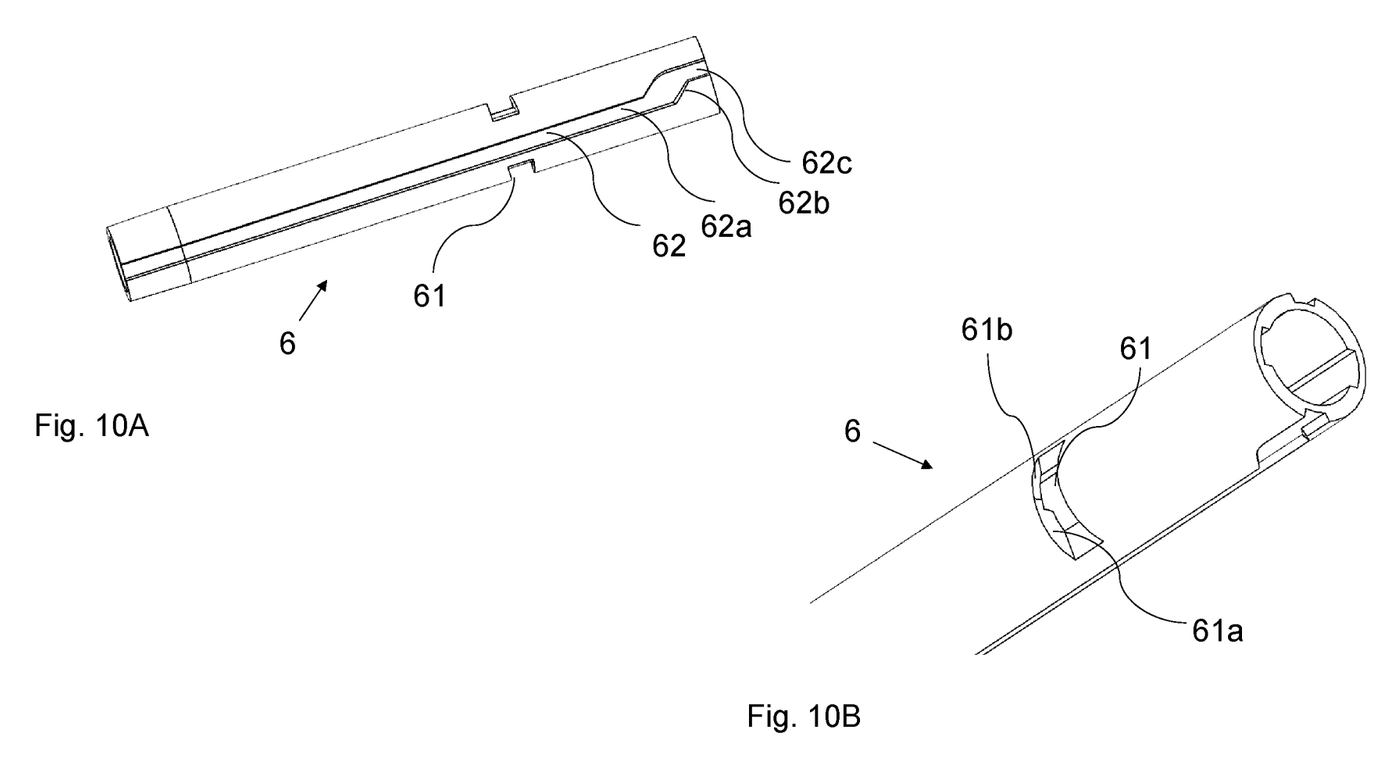
FIG. 10A displays a plunger rod of the drive mechanism of FIG. 1.
FIG. 10B displays a plunger rod of the drive mechanism of FIG. 1.

The drive mechanism may further comprises a plunger rod 6, as shown in FIG. 10A. The plunger rod 6 is configured to apply an axial biasing force on the stopper of the medicament container 5 in the proximal direction in relation to the medicament container 5. Such that the medicament contained within the medicament container 5 can thereby be delivered to the user of the medicament delivery device.

The drive assembly 2 may further comprises a plunger holder 23, configured to transfer the axial force applied on the drive assembly 2 to the stopper of the medicament container 5, the stopper of the medicament container 5 is thereby being axially moved toward the proximal direction in relation to the medicament container 5 during the medicament delivery operation of the medicament delivery device. Such arrangement is achieved by a releasable engagement between the plunger holder 23 and the plunger rod 6.

Figure 11:
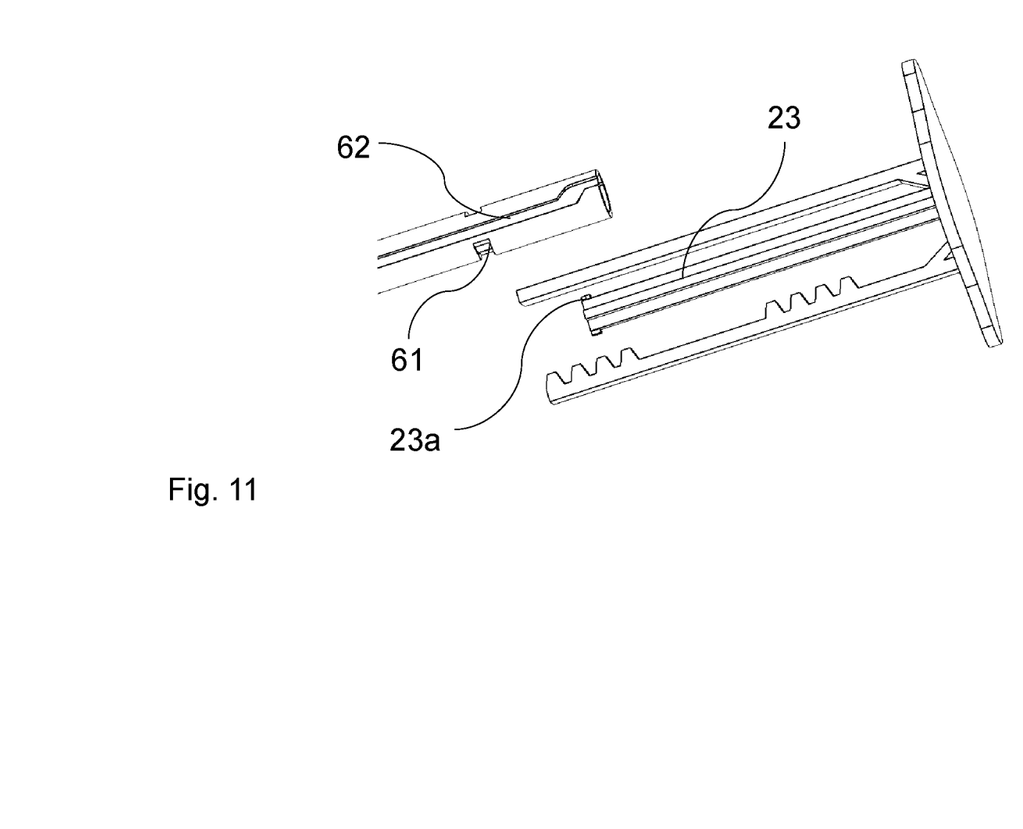
FIG. 11 displays a drive assembly of the drive mechanism of FIG. 1 and the plunger rod.

The plunger holder 23 is configured to engage with the plunger rod 6 in the initial position of the medicament delivery device and during the medicament delivery operation of the medicament delivery device. During the medicament delivery operation, the drive assembly 2 is moved axially towards the proximal direction of the housing 1. The force applied on the drive assembly 2 transfer to the stopper of the medicament container, therefore proximally moves the stopper of the medicament container to deliver the contained medicament. Once the stopper of the medicament container 5 has been moved into its end position, the plunger rod 6 is disengaged from the plunger holder 23, such that the drive assembly 2 can continuously move to the proximal direction in relation to the housing 1 without transferring the force to the stopper of the medicament container. The continuously proximal movement of the drive assembly 2 moves the container carrier 3 and the medicament container 5 back to its initial position by the mechanism as mentioned above. Such engagement and disengagement between the plunger rod 6 and the plunger holder 23 can be achieved by an engaging element 61 on the plunger rod 6 and a counter engaging element 23a on the plunger holder 23, as shown in FIG. 11; and by a guide track 62 on the plunger rod and a guide pin on the inner surface of the container carrier 3 (not shown); and will be explained in detail later.

The plunger rod 6 comprises a hollow and longitudinally extending central cavity in which the plunger holder 23 is partially positioned. The counter engaging element 23a is configured to releasably engage with the engaging element 61 of the plunger rod 6 from the interior of the plunger rod 6. As shown in FIG. 10B, the engaging element 61, preferably a recess, comprises a proximal end edge 61a configured to axially align and engage with the counter engaging element 23a when the counter engaging element 23a is engaged with the counter engaging element 23a; and a disengaging edge 61b angularly offsets in relation to the proximal end edge 61a. Preferably, the counter engaging element 23a is a radially outwards extending protruding rib arranged on the outer surface of the plunger holder 23. The proximal end edge 61a is a radially inwards extending ledge. The radially inwards extending length of the disengaging edge 61b is less than the radially inwards extending length of proximal end edge 61a.

The counter engaging element 23a comprises a radially outwards extending length which is overlapping the radially inwards extending length of the proximal end edge 61a; and is free from overlapping with the radially inwards extending length of the disengaging edge 61b. Therefore, once the counter engaging element 23a is aligned with the proximal end edge 61a, the counter engaging element 23a is able to rest on the proximal end edge 61a, such that the plunger holder 23 and the plunger rod 6 is releasably engaged and are able to move together in the proximal direction in relation to the housing 1. Once the counter engaging element 23a is aligned with the disengaging edge 61b, the counter engaging element 23a will be free from being axially supported in the proximal direction of the plunger rod 6, such that the plunger holder 23 is axially movable in relation to the plunger rod 6.

The guide track 62 on the plunger rod 6 comprises a first linear groove 62a, a second linear groove 62c, which is distally positioned and linearly offset in relation to the first linear groove 62a, and a ramp turning groove 62b connecting the first linear groove 62a and the second linear groove 62c.

It should be noted that, alternatively, the second linear groove 62c can be removed and the ramp turning groove 62b can extend to the distal end edge of the outer surface of the plunger rod 6.

Figure 12A:
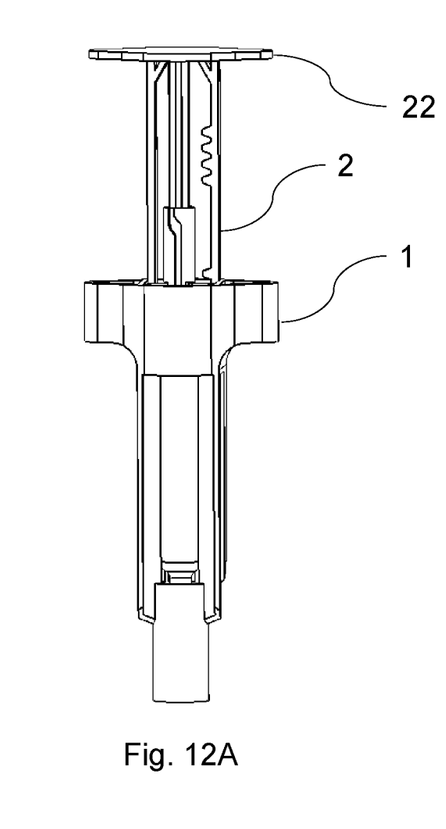
FIG. 12A displays the operation sequence of the drive mechanism of FIG. 1.
Figure 12B:
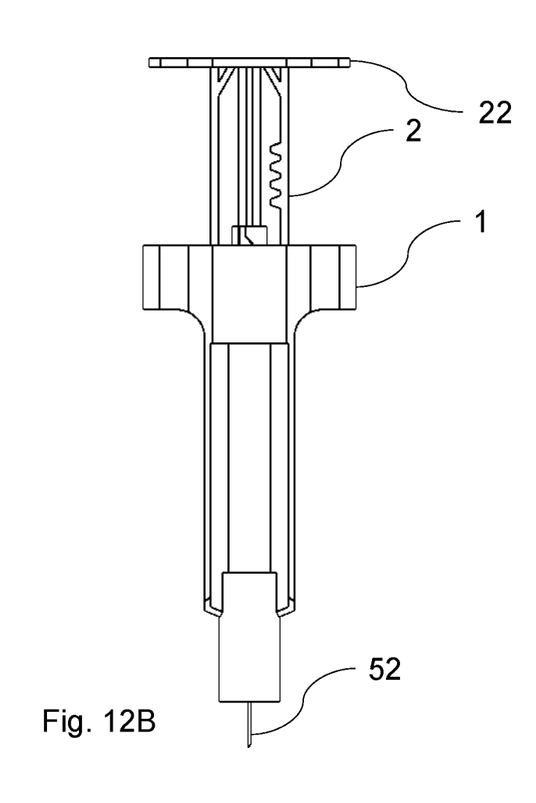
FIG. 12B displays the operation sequence of the drive mechanism of FIG. 1.

In the initial position of the medicament delivery device, which is the position before a medicament delivery operation is initiated and the medicament delivery member is hidden within the housing 1, the guide pin on the inner surface of the container carrier 3 is positioned within the first linear groove 62a of the plunger rod 6, and the counter engaging element 23a of the plunger holder 23 is rest on the proximal end edge 61a of the plunger rod 6, such that the proximally axially movement of the drive assembly 2 also causes the plunger rod 6 to move axially in the proximal direction in relation to the housing 1, as shown in FIG. 12A. To initiate the whole operation sequence of the medicament delivery device, the user needs to aim the proximal end of the housing 1 to the medicament delivery site, and apply an axial proximal force on the pushing element 22. The axial proximal force applied on the pushing element 22 turns into the axial movement of the drive assembly 2. With the proximal axial movement of the drive assembly 2, the rack arm 21 of the drive assembly 2 rotates the cogwheel 4 through the engagement between the first set of rack teeth 21a and the plurality cogs 45 of the cogwheel 4 as mentioned above, the container carrier 3 and the medicament container 5 are also moved towards the proximal direction in relation to the housing 1, since both the plunger rod 6 and the medicament container 5 are axially moved in the proximal direction in relation to the housing 1, the plunger rod 6 is free from applying the axial biasing force on the stopper of the medicament container 5. Once the medicament container 5 and the container carrier 3 reaches their most proximal position, which may be defined by the diameter of the cogwheel or the circular moving path of the connecting member 44 associated with the inner support 12 of the housing 1, a medicament delivery member 52 is properly exposed, as shown in FIG. 12B. The medicament delivery device now is ready for initiating the medicament delivery operation. Since the counter connecting member 32 of the container carrier 3 is connected to the connecting member 44, once the connecting member 44 reaches to its most proximal position, and/or the container carrier 3 is supported by the inner support 12 of the housing, the further proximal movement of the container carrier 3 is prevented.

Since the container carrier 3 and the medicament container 5 is no longer movable in the proximal direction in relation to the housing 1, the continuous axial movement of the drive assembly 2 and the plunger rod 6 in the proximal direction in relation to the housing 1 causes the plunger rod 6 to apply an axial biasing force on the stopper of the medicament container 5 and moves the stopper of the medicament container 5 towards the proximal direction in relation to the medicament container 5. The medicament contained within the medicament container 5 is thereby delivered to the user of the medicament delivery device.

The axial travel length of the guide pin on the first linear groove 62a and the ramp turning groove 62b may be designed depending on the volume of the contained medicament The further axial movement of the drive assembly 2 causes the plunger rod 6 to rotate when the guide pin of the container carrier 3 passes ramp turning groove 62b, such that the disengaging edge 61b is aligned with counter engaging element 23a, allowing the plunger holder 23 to disengage from the plunger rod 6.

Figure 12C:
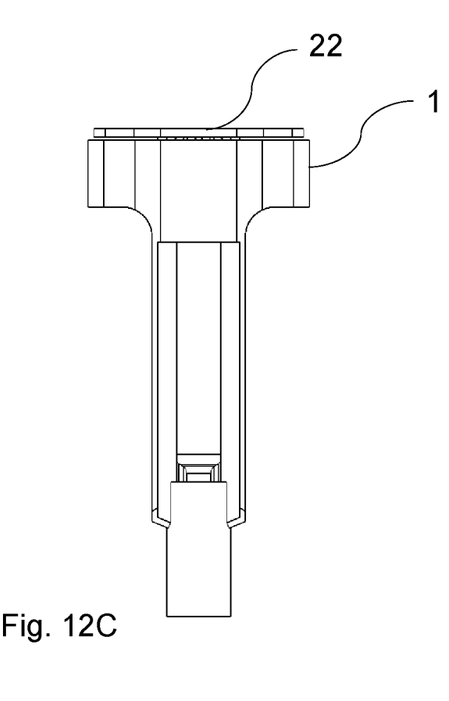
FIG. 12C displays the operation sequence of the drive mechanism of FIG. 1.

Once the plunger holder 23 is disengaged from the plunger rod 6, the drive assembly 2 continuously moves to the proximal direction in relation to the housing 1 without axially moving the plunger rod 6. The axial continuously movement of the drive assembly 2 and the rack arm 21 rotates the cogwheel 4 through the engagement between the second set of rack teeth 21b and the plurality cogs 45 of the cogwheel 4, since the counter connecting member 32 of the container carrier 3 is connected to the connecting member 44, when the connecting member 44 rotates together with the cogwheel 4 from its most proximal position to its most distal position, the connecting member 44 moves the container carrier 3 and the medicament container 5 back to the initial position. As shown in FIG. 12C, the medicament delivery member is thereby moved back into the housing 1 with the medicament container 5 and the container carrier 3, such that access to the medicament delivery member 52 by the user is prevented and thereby the injury or infection caused by accessing the used medicament delivery member can be prevented. When the pushing element 22 moved to couple with the housing 1 by the user, the user is aware that the whole operation sequence of the medicament delivery device is completed and the medicament delivery device can be removed from the medicament delivery site.

It should be noted that, the drive assembly can also be used with a medicament container with a plunger and a plunger rod. In this embodiment, the plunger rod 6 of the drive mechanism can be rearranged with a larger diameter and a shorter axial length, such that the plunger rod 6 of the drive mechanism can be distance from the stopper of the medicament container. The plunger rod of the medicament container can be arranged within the plunger rod 6 of the drive mechanism, and axially fixed to each other.

When the second set of rack teeth 21b reach to the smooth portion 46 of the cogwheel, the second set of rack teeth 21b can no longer rotate the cogwheel 4. Since both second set of rack teeth 21b or the first set of rack teeth 21a can now only pass through the smooth portion 46 of the cogwheel, the backward or forward linear movement of the rack arm 21 can no longer cause the rotation of the cogwheel, the rack arm 21 is thereby decoupled from the cogwheel. Such that reusing of the medicament delivery device is prevented. Further, the drive assembly 2 may further comprises a final position locking member configured to interact with a counter final position locking member arranged on the inner surface of the housing 1, such that the drive assembly 2 can be axially fixed to the housing 1 with the distal surface of the pushing element 22 exposed from the housing 1, as shown in FIG. 12C. The engagement between the final position locking member and the counter final position locking member can be arranged as snap fitting structure, form fitting structure or force fitting structure, to prevent the medicament delivery device being reused.

It should be noted that, the smooth portion 46 of the cogwheel 4 and the final position locking mechanism performed by the final position locking member and the counter final position locking member can be both implemented in the medicament delivery device or only using one of them as the reusing prevention mechanism in the medicament delivery device.

It should be noted that, the drive assembly can be arranged to associate with a power source, such as spring, gas canister or electric motor. In this embodiment, the pushing element 22 can completely arranged within the housing 1, such that the user cannot access to the pushing element 22; and the pushing element 22 be connected to the power source. Further, the rack arm 21, the user accessible pushing element 22 and the plunger holder 23 arranged on the drive assembly 2 can be all formed as one single component, or as all separate components or some are integral together and some are separate components.

The inventive concept has been described above with reference to a few examples. However, as is readily appreciated by a person skilled in the art, other embodiments than the ones disclosed above are equally possible within the scope of the inventive concept, as defined by the appended claims.

The invention claimed is:

1. A drive mechanism for a medicament delivery device, the drive mechanism comprising:
    a housing having a proximal end and a distal end;
    a container carrier arranged within the housing and being axially movable in relation to the housing;
    a drive assembly partially arranged within the housing and being axially movable in relation to the housing; and wherein the drive assembly comprises a proximally extended rack arm;
    a cogwheel arranged within the housing and being rotatable but axially fixed in relation to the housing; wherein the cogwheel is selectively coupled to the rack arm through a tangential engagement with a first set of rack teeth or a second set of rack teeth which are arranged on the rack arm;
    wherein the first set of rack teeth or the second set of rack teeth forces the cogwheel to rotate when the drive assembly is axially moved towards the proximal end in relation to the housing;
    wherein the cogwheel further comprises a connecting member configured to connect to a counter connecting member which is arranged on the container carrier such that a rotational movement of the cogwheel is converted into a linear movement of the container carrier.

2. The drive mechanism according to claim 1, wherein the drive assembly is rotationally fixed in relation to the housing.

3. The drive mechanism according to claim 1, wherein the container carrier is moved towards the proximal end in relation to the housing when the cog wheel is rotated by the first set of rack teeth and is moved towards the distal end in relation to the housing when the cog wheel is rotated by the second set of rack teeth while the drive assembly is moved towards the proximal end in relation to the housing.

4. The drive mechanism according to claim 1, wherein the connecting member is a protruded pin perpendicularly arranged in relation to an edge of the cogwheel; wherein the counter connecting member is a traverse recess; and wherein the protruded pin is arranged in the traverse recess.

5. The drive mechanism according to claim 1, wherein the first set of rack teeth is discrete proximally arranged in relation to the second set of rack teeth.

6. The drive mechanism according to claim 1, wherein the drive assembly further comprises a user accessible pushing element; such that the proximally axial movement of the drive assembly is created by a manually proximal pushing action applied onto the pushing element by the user.

7. The drive mechanism according to claim 1, wherein the drive assembly is axially biased in a proximal direction by a drive unit.

8. The drive mechanism according to claim 1, the first set of rack teeth and the second set of rack teeth are arranged to rotate the cogwheel in the same rotation direction.

9. A medicament delivery device comprising:
   a medicament container; and
   a drive mechanism comprising:
      a housing having a proximal end and a distal end;
      a container carrier arranged within the housing and being axially movable in relation to the housing;
      a drive assembly partially arranged within the housing and being axially movable in relation to the housing; and wherein the drive assembly comprises a proximally extended rack arm;
      a cogwheel arranged within the housing and being rotatable but axially fixed in relation to the housing; wherein the cogwheel is selectively coupled to the rack arm through a tangential engagement with a first set of rack teeth or a second set of rack teeth which are arranged on the rack arm;
   wherein the first set of rack teeth or the second set of rack teeth forces the cogwheel to rotate when the drive assembly is axially moved towards the proximal end in relation to the housing;
   wherein the cogwheel further comprises a connecting member configured to connect to a counter connecting member which is arranged on the container carrier such that a rotational movement of the cogwheel is converted into a linear movement of the container carrier.

10. The medicament delivery device according to claim 9, wherein the medicament container arranged with a medicament delivery member on its proximal end and contained a medicament therein;
   wherein the medicament container is axially fixed to the container carrier; and wherein the medicament container comprises a plunger configured to be moved towards the proximal end to expel the contained medicament through the medicament delivery member.

11. The medicament delivery device according to claim 10, wherein the drive assembly further comprises a plunger holder associated with the stopper of the medicament container; wherein the proximal movement of the drive assembly moves the plunger towards the proximal end through the plunger holder.

12. The medicament delivery device according to claim 11, wherein the proximal movement of the drive assembly sequentially causes the first set of rack teeth rotate the cogwheel, the plunger moves proximally to expel the medicament and the second set of rack teeth rotate the cogwheel.

13. A drive mechanism for a medicament delivery device, the drive mechanism comprising:
   a housing having a proximal end and a distal end;
   a drive assembly rotatably fixed relative to the housing and axially movably within and relative to the housing, where the drive assembly comprises a plunger holder and a proximally extended rack arm;
   a container carrier configured to engage and hold a container of medicament, where movement of the rack causes axial movement of the container carrier relative to the housing; and
   a cogwheel engaged with the container carrier and being rotatable but axially fixed relative to the housing, where the cogwheel comprises a plurality of cogs configured to engage a first set of rack teeth on the rack arm and then subsequently a second set of rack teeth on the rack arm as the rack arm moves proximally relative to the housing,
   wherein the proximal movement of the rack arm causes the cogwheel to rotate which causes the container carrier to first move proximally and then move distally.

14. The drive mechanism of claim 13, wherein the cogwheel further comprises a connecting member configured to connect to a counter connecting member which is arranged on the container carrier such that a rotational movement of the cogwheel is converted into a linear movement of the container carrier.

15. The drive mechanism of claim 13, wherein the rack arm comprises a first set of rack teeth positioned on a proximal end of the rack arm.

16. The drive mechanism of claim 15, wherein the rack arm comprises the second set of rack teeth positioned on a distal end of the rack arm such that the there are no rack teeth between the first set of rack teeth and the second set of rack teeth.

17. The drive mechanism of claim 16, wherein when the plunger holder is moved axially relative to the housing in a distal direction the rack arm decouples from the cogwheel when the first set of rack teeth disengage from cogwheel while the plunger holder continues to move axially, where disengagement of the first set of rack teeth from the cogwheel stops the axial movement of the container carrier and allows continued axial movement of the plunger holder relative to the housing and the container carrier.

18. The drive mechanism of claim 16, wherein further axial movement of the plunger holder causes the second set of rack teeth to engage and rotate causing the container carrier to move axially in a distal direction relative to the housing and the plunger holder.

19. The drive mechanism of claim 13, wherein the drive assembly further comprises a user accessible pushing element operatively connected to the plunger holder such that the proximally axial movement of the plunger holder is created by a manually proximal pushing action applied onto the pushing element by the user.

20. The drive mechanism of claim 13, wherein the drive assembly is axially biased in a proximal direction by a spring, gas canister or electric motor.

* * * * *